(12) United States Patent
Park et al.

(10) Patent No.: US 12,251,553 B1
(45) Date of Patent: Mar. 18, 2025

(54) SMART BAND FOR TREATING WOUNDS AND INJURIES CAPABLE OF SELF-TREATMENT, AND SMART BAND CONTROL SYSTEM INCLUDING SAME

(71) Applicant: ENERGY MINING Co., Ltd., Suwon-si (KR)

(72) Inventors: Hyun Moon Park, Gunpo-si (KR); Young Min Cho, Seongnam-si (KR)

(73) Assignee: ENERGY MINING Co., Ltd., Suwon-si (KR)

( * ) Notice: Subject to any disclaimer, the term of this patent is extended or adjusted under 35 U.S.C. 154(b) by 0 days.

(21) Appl. No.: 18/745,034

(22) Filed: Jun. 17, 2024

(30) Foreign Application Priority Data

Aug. 24, 2023 (KR) .................... 10-2023-0110967

(51) Int. Cl.
  *A61N 1/04* (2006.01)
  *A61N 1/36* (2006.01)
(52) U.S. Cl.
  CPC .......... *A61N 1/0468* (2013.01); *A61N 1/0492* (2013.01); *A61N 1/36031* (2017.08)
(58) Field of Classification Search
  CPC . A61N 1/0468; A61N 1/0492; A61N 1/36031
  See application file for complete search history.

(56) References Cited

U.S. PATENT DOCUMENTS

| | | | | |
|---|---|---|---|---|
| 2010/0174343 A1* | 7/2010 | Andino | ................ | A61N 1/326 607/50 |
| 2016/0344094 A1* | 11/2016 | Singh | ................ | A61N 1/3787 |
| 2017/0156662 A1* | 6/2017 | Goodall | ................ | A61N 2/002 |
| 2021/0163935 A1* | 6/2021 | Castor | ................ | C07K 14/521 |
| 2022/0155276 A1* | 5/2022 | Scherer | ............ | A61F 13/00051 |
| 2022/0313610 A1* | 10/2022 | Castor | ................ | A61K 9/5123 |

FOREIGN PATENT DOCUMENTS

| | | |
|---|---|---|
| JP | 2014-533182 A | 12/2014 |
| KR | 101790081 B1 | 10/2017 |
| KR | 102570162 B1 | 8/2023 |

OTHER PUBLICATIONS

Chandra et al., Microbial lipases and their industrial applications: a comprehensive review, Aug. 26, 2020, Nature (Year: 2020).*

* cited by examiner

*Primary Examiner* — Catherine M Voorhees
(74) *Attorney, Agent, or Firm* — Studebaker Brackett PLLC

(57) ABSTRACT

The present disclosure relates to a smart band for treating wounds and injuries including: an electrode band module configured to be attached to a target area of a user; a communication module connected to the electrode band module and having a wireless power transmission function; an electrode module arranged on the electrode band module, made of a time-sensitive material, and forming an electric field that electrically stimulates the target area and evaporates exudate of the target area by the power supplied from the communication module; and a processor sensing a supersaturated state or an unsaturated state of the exudate, and controlling the communication module and the electrode module, wherein the processor, upon determining that the exudate is in the supersaturated state, controls the communication module and the electrode module to form the electric field.

13 Claims, 11 Drawing Sheets

200

SMART BAND FOR TREATING WOUNDS AND INJURIES CAPABLE OF SELF-TREATMENT, AND SMART BAND CONTROL SYSTEM INCLUDING SAME

CROSS-REFERENCE TO RELATED PATENT APPLICATION

This application claims the benefit of Korean Patent Application No. 10-2023-0110967, filed on Aug. 24, 2023, in the Korean Intellectual Property Office, the disclosure of which is incorporated herein in its entirety by reference.

BACKGROUND OF THE PRESENT INVENTION

Field of the Present Invention

The present invention relates to a smart band for treating wounds and injuries utilizing wired or wireless power of a personal or portable device without visiting a hospital, and a smart band control system including the same, thereby accelerating wound treatment speed by applying electrical stimulation to the wound area, applying optimal wound treatment methods according to the wound, and protecting the wound area from the outside.

Background Art

In wound treatment, methods of applying electrical stimulation are being used. Minute electrical stimulation enhances the proliferation and differentiation capabilities of fibroblasts, thereby accelerating wound resilience.

In a case of using electrical stimulation to quickly treat wounds, since there is a difference in size and deviation of external resistance of various invasive chemical substances emitted from the wound or biological resistance depending on fibrin and the invasive chemical substances must be continuously absorbed and replaced, it is difficult to achieve significant effects.

Therefore, directly applying electrode stimulation inside a wound area is most effective, however, the method that directly applies electrode stimulation to the inside of the wound require surgical operations or wearable or fixed devices, so it lowers convenience and cost-effectiveness in wound treatment from the patient's perspective. Accordingly, there is a demand for products and control methods that are compact yet efficiently stimulate the wound internally and facilitate wound recovery.

PATENT LITERATURE

Patent Documents

Patent Document 1: Korean Patent No. 10-1790081 (Oct. 26, 2017)

SUMMARY OF THE PRESENT INVENTION

Accordingly, the present invention has been made to solve the above-mentioned problems occurring in the prior arts, and it is an objective of the present invention to provide a smart band for treating wounds and injuries and a smart band control system including the same, which can accelerate oxidation and reduction reactions by applying electrical stimulation to wounds, and vaporize supersaturated invasive substances at a user's target area, thereby preventing the delay in wound recovery caused by the supersaturated invasive substances at the user's target area.

The objectives of the present disclosure are not limited to those mentioned above, and other objectives not mentioned herein will be clearly understood by those skilled in the art from the following description.

To accomplish the above object, according to the present invention, there is provided a smart band for treating wounds and injuries including: an electrode band module attached to a user's target area; a communication module connected to the electrode band module and having a wireless power transmission function; an electrode module arranged on the electrode band module, made of a time-sensitive material, and forming an electric field that electrically stimulates the target area and evaporates exudate of the target area by the power supplied from the communication module; and a processor sensing a supersaturated state or an unsaturated state of the exudate, and controlling the communication module and the electrode module, wherein the processor, upon determining that the exudate is in the supersaturated state, controls the communication module and the electrode module to form the electric field.

Moreover, the smart band further includes: a ground connection unit ground-connected to the target area; and a feedback current measurement unit electrically connected to the ground connection unit, and measuring a feedback current entering and returning to the ground connection unit, wherein the processor determines the supersaturated state or the unsaturated state of the exudate based on the feedback current measured by the feedback current measuring part.

Furthermore, further includes: a the smart band temperature sensor provided on the communication module to measure the temperature of the target area, wherein the processor, if a temperature measurement value measured by the temperature sensor exceeds a reference temperature, verifies the exudate as being in the supersaturated state, and if the temperature measurement value is below the reference temperature, verifies the exudate as being in the unsaturated state.

Additionally, if the state of the exudate determined by the feedback current measurement unit differs from the state determined by the temperature sensor, the processor re-measures the feedback current through the feedback current measurement unit to re-determine the supersaturated state or the unsaturated state of the exudate.

In addition, the smart band further includes: a humidity sensing unit sensing the humidity of the target area, wherein the processor verifies the exudate as being in the unsaturated state if the humidity sensed by the humidity sensing unit is below a reference humidity, and verifies the exudate as being in the supersaturated state if the humidity sensed exceeds the reference humidity.

Moreover, if the state of the exudate determined by the feedback current measurement unit differs from the state determined by the humidity sensing unit, the processor re-measures the feedback current through the feedback current measurement unit to re-determine the supersaturated state or the unsaturated state of the exudate.

Furthermore, the smart band further includes: a charge measurement unit electrically connected to the ground connection unit and measuring the charge characteristics of the target area through the ground connection unit, wherein the processor, if the charge measured by the charge measurement unit at the target area is negative, determines the exudate as being in the supersaturated state, and if the charge measured by the charge measurement unit at the target area is positive, determines the exudate as being in the unsaturated state.

Additionally, the electrode module includes: nanosomes receiving power from the communication module; an electrode pattern forming the electric field by the power transferred from the nanosomes; and an electrode pad coupled to the nanosomes and the electrode pattern, provided on the attachment surface of the electrode band module attached to the user's target area, and including at least one of hydrogel (gelma, chitosan, collagen, sodium, alginate, and PVA) and hydrocolloid.

In addition, the electrode pattern includes molybdenum.

Moreover, the molybdenum is formed of a thin film having a thickness of 0.1 μm to 10 μm, and has a cross-sectional area of less than 10% of the target area.

Furthermore, the smart band further includes: a molybdenum sensing unit arranged on the communication module to sense the molybdenum at the target area, wherein the processor, upon determining that the exudate is in the unsaturated state, controls the communication module and the electrode module to form an electric field to remove the molybdenum at the target area.

Additionally, the smart band further includes: a triboelectric generator arranged on the communication module to supply friction electricity generated due to friction by ultrasound irradiation to the communication module as power.

In addition, the smart band further includes: a ground connection unit ground-connected to the target area; and a feedback voltage measurement unit electrically connected to the ground connection unit to measure a feedback voltage entering and returning to the ground connection unit, wherein the processor determines the supersaturated state or the unsaturated state of the exudate based on the feedback voltage measured by the feedback voltage measuring part.

Moreover, when the smart band is removed, the electrode band module and the communication module are simultaneously separated from the target area or, after the communication module alone is separated and the electrode module is completely melt by the user's body heat, the electrode band module is separated.

Furthermore, the nanosome includes lipase enzyme.

Other specific details of the present invention are included in the detailed description and drawings.

The smart band for treating wounds and injuries and the smart band control system including the same can accelerate oxidation and reduction reactions by applying electrical stimulation to wounds, and vaporize supersaturated invasive substances at a user's target area, thereby preventing the delay in wound recovery caused by the supersaturated invasive substances at the user's target area.

The advantages of the present disclosure are not limited to the above-mentioned advantages, and other advantages, which are not specifically mentioned herein, will be clearly understood by those skilled in the art from the following description.

DETAILED DESCRIPTION OF THE PREFERRED EMBODIMENT

Figure 1A:
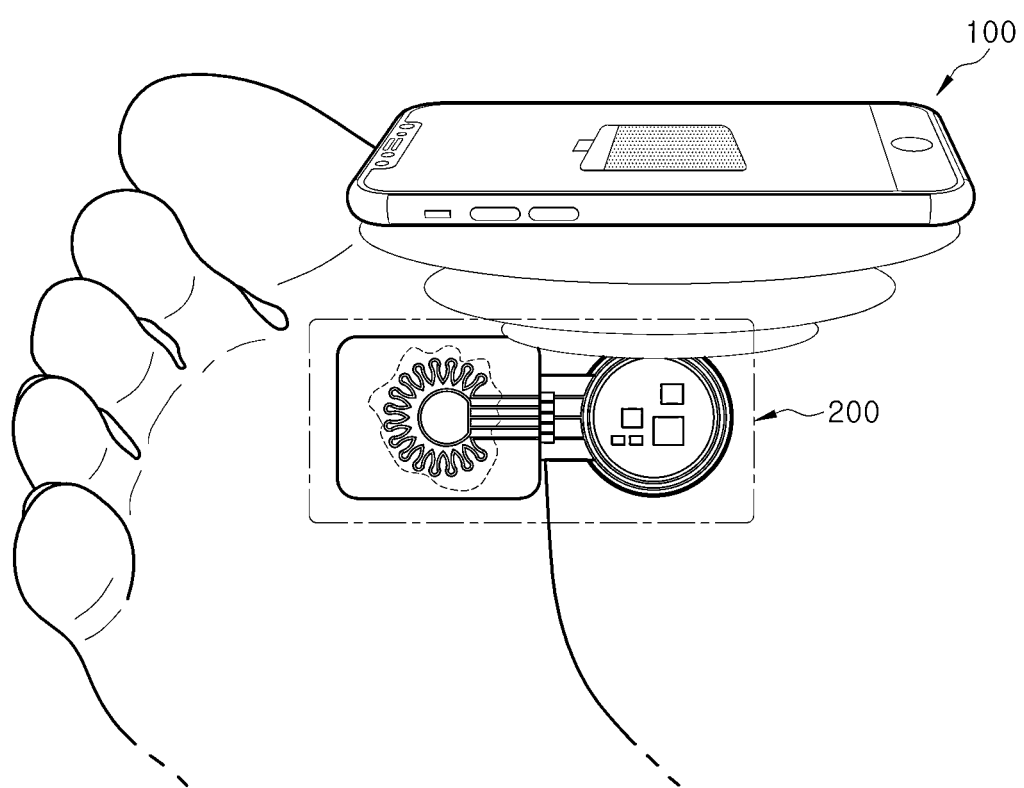
FIG. 1A is a perspective view illustrating a smart band control system for treating wounds and injuries capable of self-treatment according to an embodiment of the present invention.

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Terms, such as "below," "beneath," "lower," "above," "upper," and the like, which have spatially relative concepts, may be used to facilitate correlation between one component and other components, as illustrated in the drawings. Such spatially relative terms should be understood as terms including different directions of components during use or operation, in addition to the direction illustrated in the drawings. For example, if the components illustrated in the drawings are turned upside down, the components described as "below" or "beneath" may be placed "above" of other components. Thus, the exemplary term "under" may include all of the directions, "below" and "above". The components may be oriented in other directions, so that the spatially relative terms can be interpreted according to the orientation.

Hereinafter, a smart band system for treating wounds and injuries according to an embodiment of the present invention will be described.

Figure 1B:
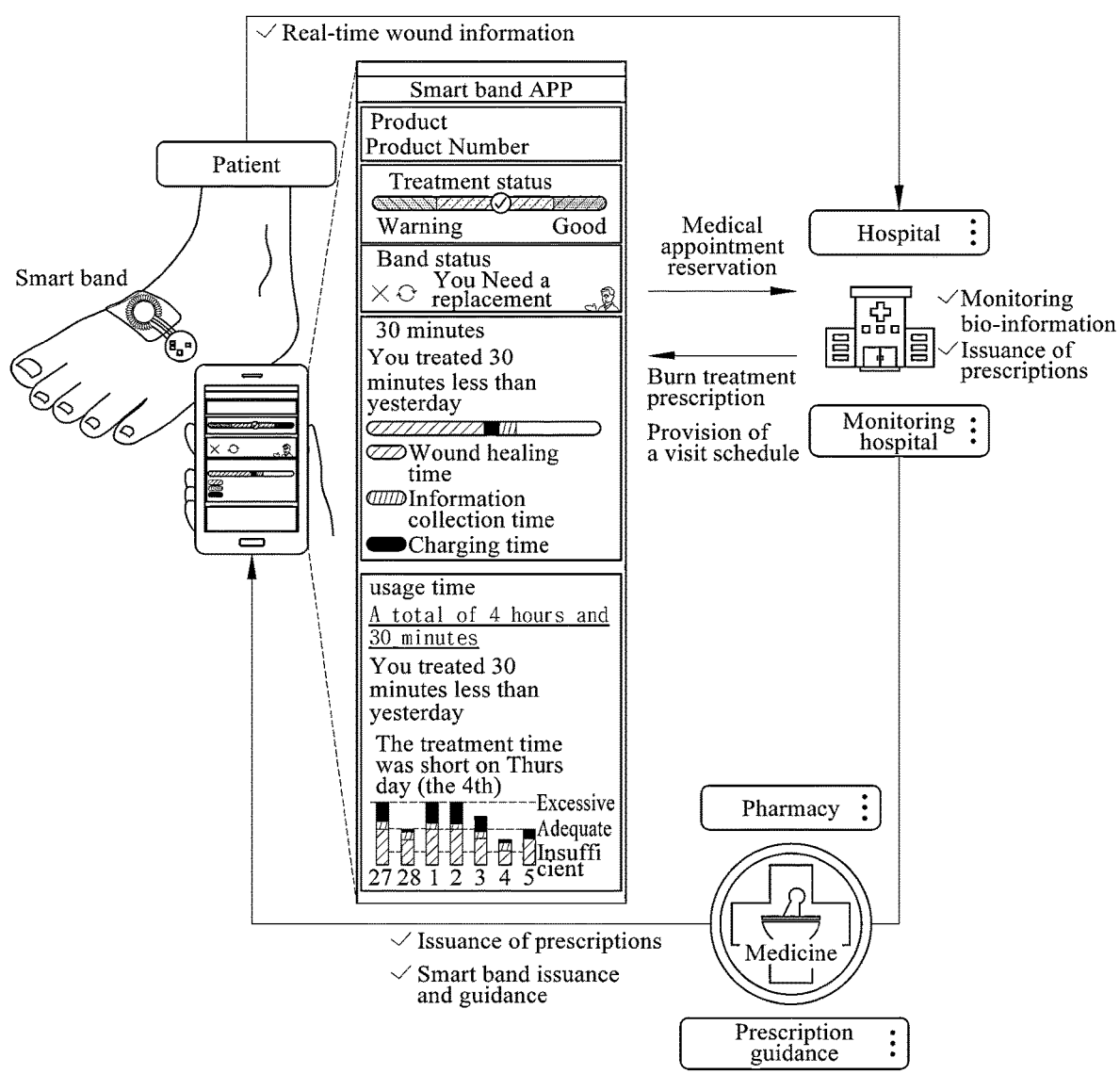
FIG. 1B is a schematic diagram illustrating an use example of the smart band control system for treating wounds and injuries capable of self-treatment according to the embodiment of the present invention.
Figure 1C:
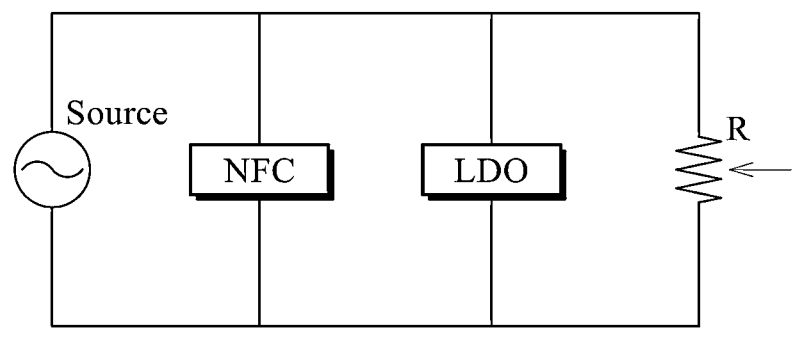
FIG. 1C is a schematic diagram illustrating the biological resistance depending on electrical stimulation in the smart band control system for treating wounds and injuries capable of self-treatment according to the embodiment of the present invention.

FIG. 1A is a perspective view illustrating a smart band control system for treating wounds and injuries capable of self-treatment according to an embodiment of the present invention, FIG. 1B is a schematic diagram illustrating an use example of the smart band control system for treating wounds and injuries capable of self-treatment according to the embodiment of the present invention, and FIG. 1C is a schematic diagram illustrating the biological resistance depending on electrical stimulation in the smart band control system for treating wounds and injuries capable of self-treatment according to the embodiment of the present invention.

As illustrated in FIGS. 1A to 1B, the smart band control system for treating wounds and injuries according to the embodiment of the present invention can include an electronic device 100 and a smart band 200 for treating wounds and injuries.

Referring to FIGS. 1A to 1B, the smart band control system according to an embodiment of the present invention includes an electronic device 100 and a smart band 200 for wound treatment. The smart band 200 for treating wounds and injuries can be connected with the electronic device 100 to be able to communicate with the electronic device 100.

The electronic device 100 may include any type of electronic devices that provides short-range communication (e.g., NFC) and wireless power transmission capabilities. For example, the electronic device 100 can be a device that provides power to and controls communication with the smart band by cable or wirelessly, and include smartphones, tablet PCs, smartwatches, and smart wristbands, but is not limited thereto.

The electronic device 100 can supply power to the smart band 200 using wireless or wired communication devices, and can collect information on a user's wound state from the smart band 200 for treating wounds and injuries, and transmit the information to individuals or medical professionals or places where can collect, diagnose and prescribe medical information. The electronic device 100 can receive information of remote or nearby locations through applications or programs of the electronic device 100, and control the smart band 200 for treating wounds and injuries based on the corresponding information. Additionally, the electronic device 100 can transmit the information to remote or nearby locations through a connected IoT device.

Furthermore, the electronic device 100 can provide users with 'usage information' or a 'product mounting method' for the smart band 200 for treating wounds and injuries, and transmit the user's wound information to a hospital, and reflect the information prescribed by the hospital to control the electrical stimulation applied to the user's wound by the smart band 200, thereby enhancing the treatment effects (refer to FIG. 1B).

The electronic device 100 can provide the user with control information and charging information of the smart band 200 for treating wounds and injuries. Additionally, the electronic device 100 can acquire information about usage status, treatment status, product number, product installation method, and usage time based on the user's actions, and provide the information to the hospital through a smart terminal of the user. Accordingly, the electronic device 100 not only provides the self-treatment function for treating the user's wounds but also reflects prescription results provided from the hospital in real time to be appropriate for the user's wounds and situations, thereby providing various kinds of information, such as wound treatment, medical appointment, replacement cycles of the smart band, and the likes for the user (refer to FIG. 1B).

The smart band 200 for treating wounds and injuries can receive power from the electronic device 100. Additionally, the smart band 200 for treating wounds and injuries can be attached to a user's target area 10 to evaporate invasive substances at the user's target area 10, and apply electrical stimulation to the wound at the user's target area 10.

In general, when a biological wound is healed, there is a phenomenon where nerves and cells restore the original wound according to an electrical phenomenon known as action currents, and the granulation tissue, which contains fibroblasts serves a major role for the phenomenon, namely, serves to restore tissues by synthesizing tissue components such as collagen. In this case, minute electrical stimulations can accelerate tissue restoration by enhancing the proliferation and differentiation abilities of fibroblasts.

However, when the wound is accelerated by external stimulations such as electrical stimulation, since the size and deviation of external resistance of various invasive chemical substances emitted from the wound or biological resistance depending on fibrin are uneven, it is difficult to achieve effective results. Therefore, the most effective method is to directly stimulate the inside of the wound through electrodes. However, to directly apply electrical stimulation to the inside of the wound through the electrodes requires surgical devices and instruments which are more complex than portable devices and instruments, but it reduces practicality. So, a method of treating wounds with devices based on wound dressing materials that use negative pressure to reduce biological resistance variations through exudate discharge, and reduce biological resistance and enhance blood flow by facilitating blood flow has been used. However, except for the advantages of wound protection and wound disinfection through creation of a moist environment, the method is nearly natural treatment and is less efficient compared to the electrical stimulation method. Hence, the inventor of the present invention has continued research to accelerate the dermal layer with electricity using bio-materials with conductivity as a method of minimizing wound stimulation without surgery and without being affected by the external resistance of chemicals. As a result, the smart band 200 for treating wounds and injuries according to the embodiment of the present invention has been developed.

The smart band 200 for treating wounds and injuries according to the embodiment of the present invention may include a time-sensitive material. Here, the time-sensitive material can operate temporarily to provide electrical stimulation to the wound area and can be absorbed into the body during the wound treatment process.

For example, when the smart band 200 for treating wounds and injuries is attached to the user's target area 10, a portion of the time-sensitive material included in the smart band 200 can be inserted into the user's target area 10, providing electrical stimulation into the wound at the target area 10.

For example, the time-sensitive material may be at least one of molybdenum (Mo), molybdenum disulfide (MoS2), tungsten disulfide (WS2), zinc oxide (ZnO), and magnesium oxide (MgO), but the present invention is not limited thereto. The time-sensitive material is capable of conducting electricity and is harmless to the human body. If the time-sensitive material applies electrical stimulation to the wound area by supplying electrical power, fibroblasts rapidly proliferate and differentiate, to rapidly restore the restoration of the dermis, thereby treating the wound area.

However, although the method can quickly restore the dermis via electrical stimulation, the recovery tension lowers to about 80% compared to the state before the wound, and the method has several problems in that also the method cannot be free from the scabs, which are formed while dried blood, pus, and exudate are dried, and the wound exudate is rapidly evaporated. That is, exudate contains macrophages that remove dead cells and foreign bodies such as bacteria, white blood cells that promote wound treatment, lysosomal enzymes, and growth factors densely packed. If such components are evaporated due to electrical stimulation, it can cause delayed wound recovery.

Particularly, electrical stimulation uses microcurrents and voltage, and the biological resistance (R) changes depending on the severity, size, and treatment progress of the user's wound. Thus, even if the same microcurrent and voltage are provided, it exhibits characteristics similar to a variable resistor (Refer to FIG. 1C). For example, if the size of the user's wound is large, the biological resistance (R) is relatively low. However, when the treatment is complete, the biological skin resistance (R) value ranges from 2.5 to 10 MΩ. Particularly, areas like the feet have high biological resistance (R), but areas like the chest have low biological resistance. The initial internal resistance in areas with large wounds can decrease to 300 to 7500, and the internal resistance increases depending on the distance from the heart.

The smart band 200 for treating wounds and injuries according to the embodiment of the present invention provides electrical stimulation within the wound through an insertion-type material to recover the dermis, and is designed to maintain a moist environment without evaporating components such as exudate, thereby providing an improved experience in wound recovery power and treatment speed.

Hereinafter, the smart band 200 for treating wounds and injuries capable of self-treatment according to an embodiment of the present invention will be described in detail.

Figure 2:
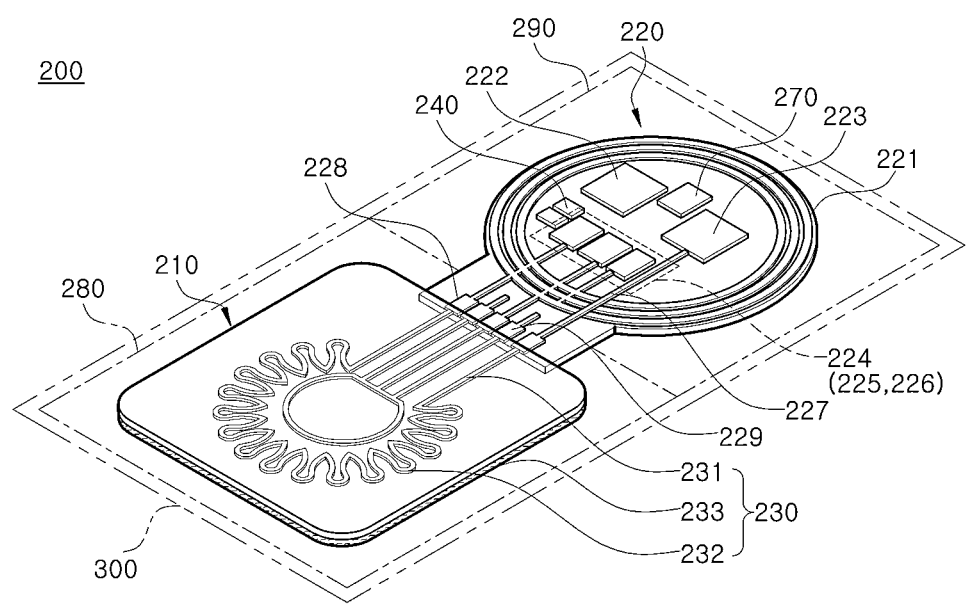
FIG. 2 is a perspective view of a smart band for treating wounds and injuries capable of self-treatment according to an embodiment of the present invention.
Figure 3:
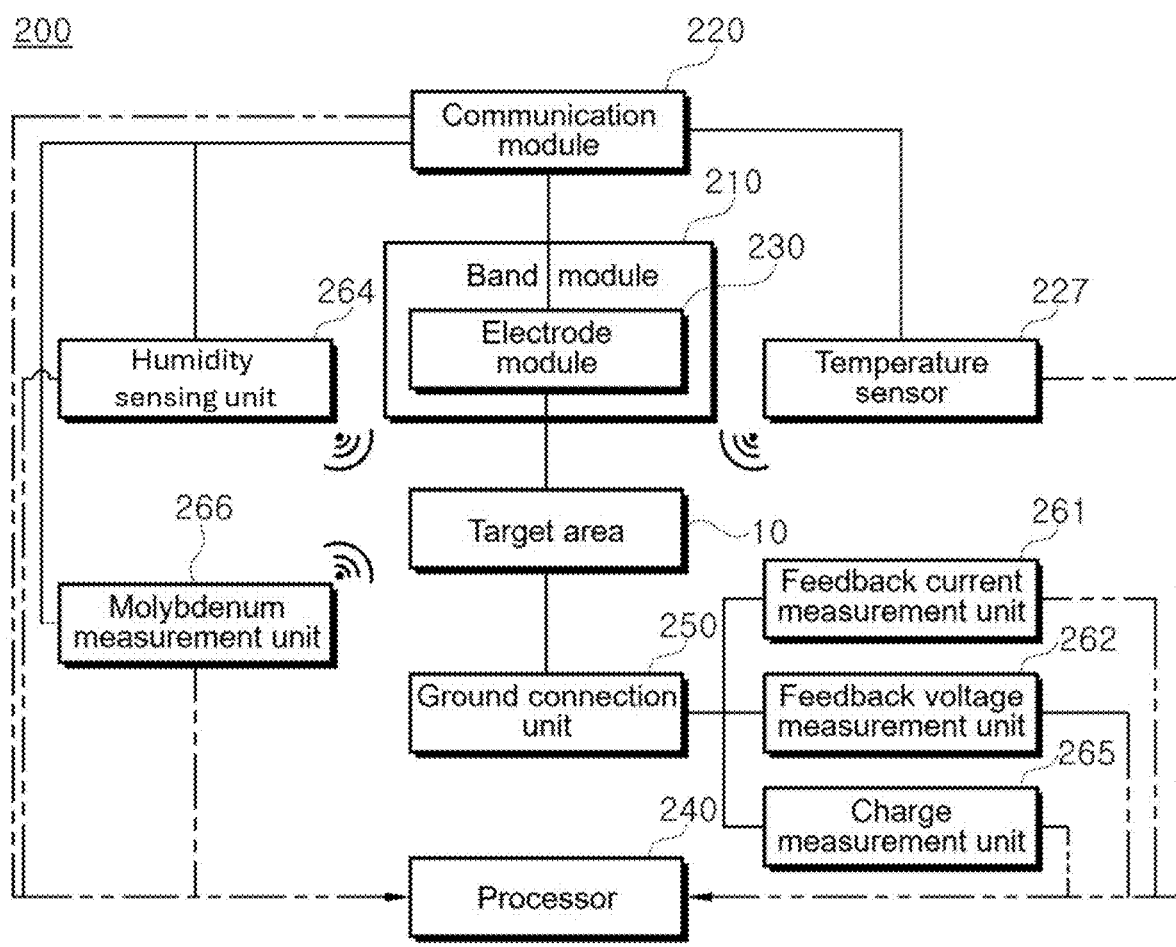
FIG. 3 is a block diagram of the smart band for treating wounds and injuries capable of self-treatment according to the embodiment of the present invention.
Figure 4:
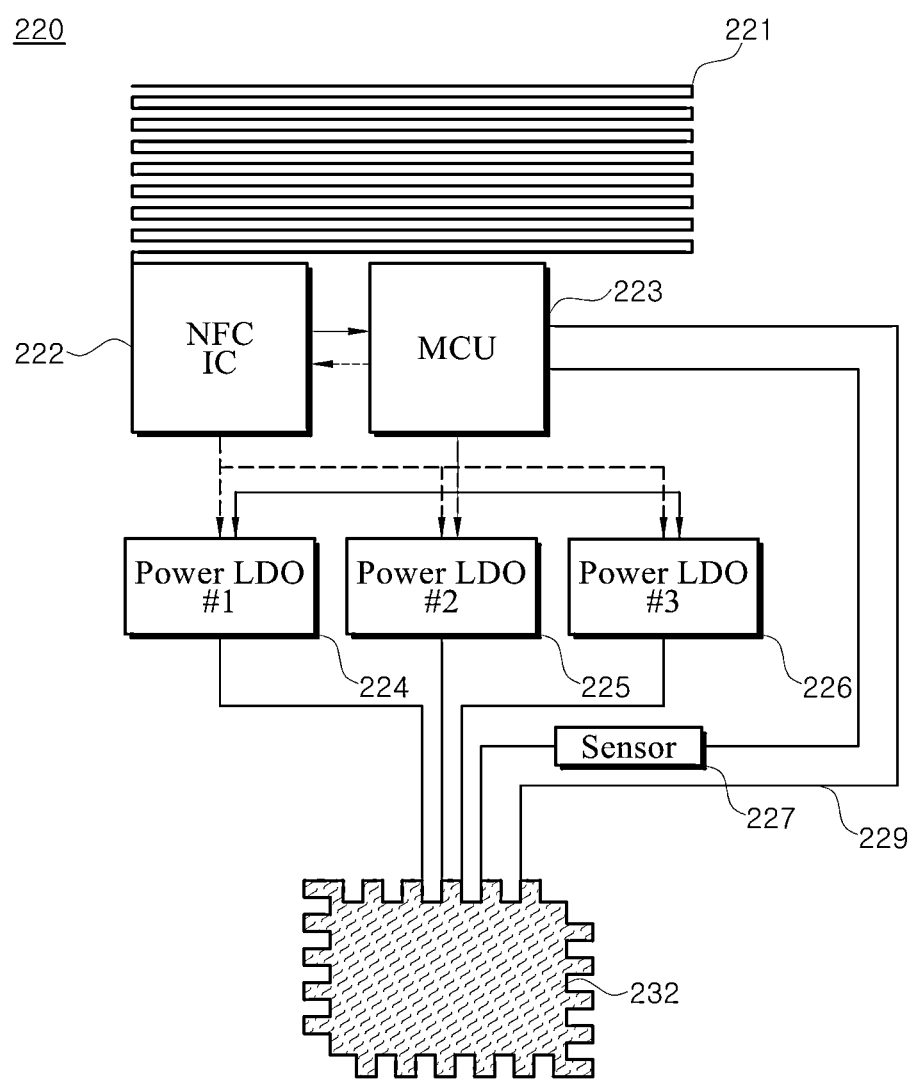
FIG. 4 is a block diagram illustrating a communication module of the smart band for treating wounds and injuries capable of self-treatment according to the embodiment of the present invention.

FIG. 2 is a perspective view of a smart band for treating wounds and injuries capable of self-treatment according to an embodiment of the present invention, FIG. 3 is a block diagram of the smart band for treating wounds and injuries capable of self-treatment according to the embodiment of the present invention, and FIG. 4 is a block diagram illustrating a communication module of the smart band for treating wounds and injuries capable of self-treatment according to the embodiment of the present invention.

As illustrated in FIGS. 2 through 4, the smart band 200 for treating wounds and injuries according to the embodiment of the present invention is divided into an electrode band 290 directly attached to the wound, and a subsidiary material 300 surrounding a smart module 280, and may include an electrode band module 210, a communication module 220, an electrode module 230, a processor 240, a temperature sensor 227, a communication module electrode 228, and a sensing unit electrode 229.

In the present invention, the user's target area 10 may be a unit of the user which includes the user's wound.

The electrode band module 210 serves to attach the electrode module 230 to the user's target area 10. For this purpose, the subsidiary material 300 is provided on one side of the electrode band module 210 to be attached to the user's target area 10. For instance, the subsidiary material 300 may be a polyurethane film, but the present invention is not limited thereto. For example, the polyurethane film can include breathable waterproof porous polyethylene, allow the passage of water vapor and air, and block droplets and external pathogens like bacteria. Alternatively, the polyurethane film may have a thickness ranging from 10 μm to 100 μm. The polyurethane film, serving as the subsidiary material 300, can be utilized to replace and remove the smart band. Specifically, since the electrode band module 210 mainly serves to maintain moisture, it is common that the nanosome 231 and electrode module 232 are absorbed into the user but the electrode band module 210 does not dissolve during the wound treatment. However, as being made from hydrocolloid materials, the electrode band module 210 can form a colloidal gel that cools the temperature and provide a refreshing sensation.

The communication module 220 may be connected to the electrode band module 210 and have a wireless power transmission function. Here, the wireless power transmission function can involve the communication module 220 supplying power to the electrode module 230.

For example, the communication module 220 may supply power from the electronic device 100 to the electrode module 230. In this case, the communication module 220 can receive power from the electronic device 100 via NFC function.

Alternatively, the communication module 220 may supply power from a triboelectric generator 270, which will be described later, to the electrode module 230.

The communication module 220 may include one or more circuit elements which enable the communication function and the wireless power transmission function. The communication module 220 can be realized using NFC technology. Additionally, under the control of the electronic device 100 or the processor 240, the communication module 220 can adjust the timing of power supply to the electrode module 230. As described above, since the duration that the communication module 220 supplies power to the electrode module 230 can be adjusted, the duration that the electrode module 230 electrically stimulates the user's target area 10 and creates an electric field for evaporating the exudate at the target area 10 can be also adjusted. For instance, the communication module 220 can be implemented as an active RFID capable of wireless power transmission and communication. Alternatively, the communication module 220 may utilize various wireless communication technologies such as Bluetooth modules, Wi-Fi modules, and wireless power transmission technologies including Qi (energy), AirFuel, WiTricity, and power matters alliance (PMA).

The communication module 220 may include an antenna 221, an NFC integrated circuit 222, an MCU 223, a first LDO regulator 224, a second LDO regulator 225, a third LDO regulator 226, a temperature sensor 227, a communication module electrode 228, and a sensing unit electrode 229. (Refer to FIG. 4)

The antenna 221 functions to wirelessly receive signals from the electronic device 100. The antenna 221 can receive radio signals at 13.56 MHz, which is at the NFC standard frequency, and can be manufactured in the form of a flexible printed circuit board (FPCB). The antenna 221 can induce electric power using energy supplied by an electric or magnetic field. For example, based on the power supplied from the electronic device 100, the antenna 221 can receive a voltage of 1.4V to 6V and a current of up to 300 mA.

The NFC integrated circuit 222 can supply power needed for the operation of the MCU 223, and power needed for the operations of the first LDO regulator 224, the second LDO regulator 225, and the third LDO regulator 226.

The MCU 223 can determine the resistance based on values input into an ADC, and based on values controlled by a smartphone, decide whether to use any one of the first LDO regulator 224 through the third LDO regulator 226 and supply the power necessary for the operation of the selected regulator. For this, the MCU 223 receives temperature information from the temperature sensor 227, and the sensing unit electrode 229 receives feedback values of the wound relative to electrical stimulation values generated from one of the first LDO regulator 224 to the third LDO regulator 226, transmits the feedback values to the MCU 223 through the ADC, and compares the output voltage and current of the corresponding LDO regulator, thereby inferring the resistance magnitude based solely on changes in voltage. The resistance value of the wound can ultimately aid to infer the degree of wound treatment, and the initial wound treatment value (degree) can be defined through remote input, not by the user but by diagnosis results as illustrated in FIG. 2.

The communication module electrode 228 is connected to the electrode pattern 232 of the time-sensitive material. The communication module electrode 228 is made from highly conductive non-time-sensitive metal, and can be removed along with the communication module 220.

The sensing unit electrode 229 is connected to the temperature sensor 227, is also made from highly conductive non-time-sensitive metal, and is removable with the communication module 220.

The temperature sensor 227 can be operated in either analog or digital mode, and is connected to the MCU 223 via analog I/O or digital I/O to provide temperature information. As illustrated in FIG. 2, the temperature sensor 227 is located as close as possible to the electrode band module 210 to accurately monitor the temperature of the wound. Here, the processor 240, if the measured temperature exceeds a standard threshold, verifies it as a saturated state of exudate at the user's target area 10, and if the measured temperature is below the standard threshold, verifies the liquid at the user's target area 10 as an unsaturated state. Here, the standard temperature for a temperature measurement value is set at 40° C.

The first LDO regulator 224 to the third LDO regulator 226 supply power to the electrode band module 210. The electrode pattern 232 forms an electric field that delivers electrical stimulation to the user's target area 10, thereby inducing wound treatment at the user's target area 10.

Each of the first LDO regulator 224 to the third LDO regulator 226 can have different specifications. In detail, each of the first LDO regulator 224, the second LDO regulator 225, and the third LDO regulator 226 handle different loads. The MCU 223 can use one or more of the first LDO regulator 224, the second LDO regulator 225, and the third LDO regulator 226 to provide appropriate treatment for the wound at the user's target area 10.

For example, the antenna 221 can receive integrated treatment information, including wound information, user information, operation time of the electrode module 230, and treatment time of the electrode module 230, from the electronic device 100. Based on the integrated treatment information received by the antenna 221, the MCU 223 controls the operation time and treatment time during which the electrode module 230 forms an electric field at the user's target area 10 and applies electrical stimulation to the user's target area 10, based on the real time clock (RTC) or the external RTC. After the stimulation, the MCU controls the time, voltage, and current for wound treatment through at least one of the first LDO regulator 224, the second LDO regulator 225, or the third LDO regulator 226 based on the electrical signal received from the electrode, thereby adjusting the intensity and duration of electrical stimulation provided by the electrode pattern 232.

Meanwhile, in the present invention, it has been described that the smart band 200 for treating wounds and injuries uses the three LDO regulators to treat wounds, but through modifications in the design of the smart band 200 (for example, changes in size of the smart band 200 for treating wounds and injuries), the number of the LDO regulators in some embodiments can be changed. For instance, the number of the LDO regulators may be one to five, but the present invention is not limited thereto.

The electrode module 230 is provided on the electrode band module 210 and is made from a time-sensitive material. The electrode module 230 forms the electric field that electrically stimulates the target area 10 and evaporates exudate at the target area 10 by utilizing power supplied from the communication module 220.

For example, the electrode pattern 232 can be made of a time-sensitive material that is electrically conductive and decomposes over time, allowing for absorption by the user. For example, the electrode module 230 may be made of a material, which is conductive and harmless to the human body, such as molybdenum (Mo), molybdenum disulfide (MoS2), tungsten disulfide (WS2), zinc oxide (ZnO), and magnesium oxide (MgO), but the present invention is not limited thereto.

Figure 5A:
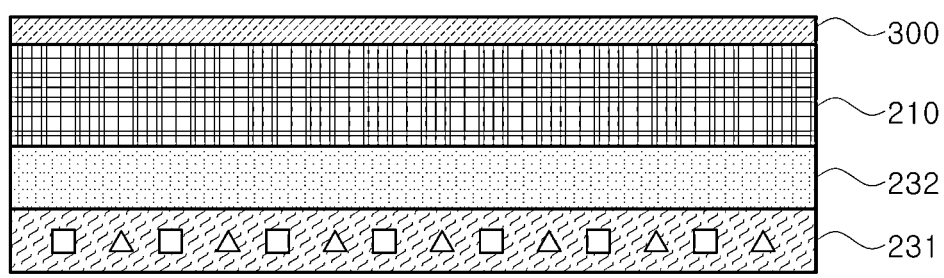
FIGS. 5A and 5B are cross-sectional views illustrating an electrode module of the smart band for treating wounds and injuries capable of self-treatment according to the embodiment of the present invention
Figure 5B:
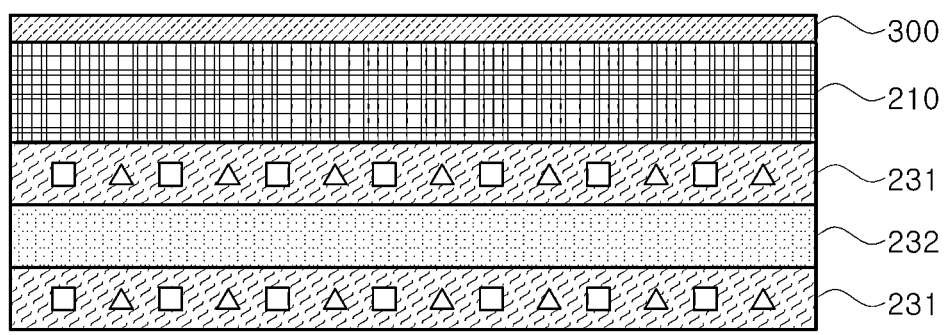

FIGS. 5A and 5B are cross-sectional views illustrating an electrode module of the smart band for treating wounds and injuries capable of self-treatment according to the embodiment of the present invention As illustrated in FIGS. 5A and 5B, the electrode module 230 may include a nanosome 231, an electrode pattern 232, and an electrode pad 233.

The nanosome 231 can be composed of at least one of biodegradable biotic containers such as PHBV [Poly (3-hydroxybutyrate-co-3-hydroxyvalerate)], PLA [Poly(lactic acid)], or PCL (Poly-Caprolactone). Triangles and rectangles of the nanosome 231 consist of enzymes that catalyze 'biocatalytic actions' by external vibrations and electrical stimulation, thereby accelerating the dissolution of the nanosome 231. Enzyme dissolve at temperature of 38 degrees or more or according to materials of the electrode module 230, so intensifies the melting point by accelerating the dissolution in response to external temperature, vibration, and electrical stimulation as the density of enzymes increases. In such a case, the nanosome 231 liquefies at several tens um scale due to electrical stimulation and thermal temperature, thereby enabling a wound treatment agent liquefied by enzyme to penetrate the wound more quickly for effective treatment and serving as an accelerator which enables the time-sensitive metal of the electrode module 230 to dissolve to the user more rapidly. The nanosome 231 may include at least one of wound fillers such as natural alginate, and polysaccharide, and synthetic materials such as polyurethane, and lipase enzyme.

The nanosome 231 receives power from the communication module 220 and can connect the electrode pattern 232 to the communication module 220. For example, the nanosome 231 can have a thickness of 50 µm to 75 µm.

In some instances, two nanosomes 231 may be provided, and the electrode pattern 232 may be interposed between the two nanosomes 231 (refer to FIG. 5B).

The electrode pattern 232 can form an electric field by the power transferred from the nanosome 231. The electric field electrically stimulates the user's target area 10 and forms the electric field to evaporate exudate at the target area 10. Therefore, the evaporation of exudate at the target area 10 can prevent the delay in wound recovery caused by the accumulation of exudate at the target area 10.

For example, the exudate evaporated by the electric field may include the user's exudate and melted material melted from the time-sensitive material by heat of the user.

For instance, depending on the size and severity of the wound, the electrode pattern 232 can have a thickness ranging from 1 µm to 25 µm. Here, the thickness of the electrode pattern 232 increases with the depth and size of the wound and becomes closer to 1 µm as the wound becomes shallower and smaller.

Additionally, the electrode pattern 232 may include molybdenum (Mo). Furthermore, the smart band according to an embodiment of the present invention may also include a molybdenum sensing unit 266. The molybdenum sensing unit 266 is provided on the communication module 220, and can sense molybdenum at the user's target area 10. Here, if determining that the exudate is in the unsaturated state, the processor 240 can control the communication module 220 and the electrode module 230 to form an electric field to remove molybdenum from the user's target area 10. In this case, the electric field at the target area 10 can play a role in promoting the removal of molybdenum.

For instance, molybdenum may be formed as a thin film with a thickness ranging from 0.1 µm to 10 µm. To prevent excessive or insufficient molybdenum, molybdenum may have the cross-sectional area of less than 10% of the user's target area.

Furthermore, the electrode pattern 232 may include gelatin and hydrogel to accelerate the melting rate due to the power and temperature delivered from the nanosome 231. Here, gelatin and hydrogel can accelerate the melting rate of fibroblasts in the granulation tissue to facilitate rapid replacement and cross-linking of collagen, thus enabling rapid differentiation and growth.

For instance, the electrode pattern 232 may have a two-dimensional structure. In this case, the electrode pattern 232 can exhibit magnetic field characteristics and can activate cells using a pulsed type faradic current for effective treatment.

For example, the hydrogel may have a plurality of tiny holes and can melt into a liquid phase by heat of the body after biological attachment.

In another example, concerning lipase enzymes used in a biodegradable container for the nanosome 231, if the biodegradable container breaks due to external heat or an electrode signal, the lipase enzymes can meet the exudate and acquire acceleration capability to be completely liquefied within an hour, thus accelerating bioabsorption and shortening the liquidation of the hydrogel.

For instance, the electrode pattern 232 may have a three-dimensional structure. In this case, the electrode pattern 232 may have characteristics of the electric field and the magnetic field, and can show more efficient wound treatment properties than using only the magnetic field.

For example, the electrode pad 233 may be attached to one side of the electrode pattern 232, and the opposite side of the electrode pad 233 may come into contact with the user's target area 10. To enhance adhesion with the user's target area 10, the opposing side of the electrode pad 233 may have a composite layer made of a rosin ester layer and a silicone layer, or a combination thereof.

The electrode pad 233 is coupled with the nanosome 231 and the electrode pattern 232 and is positioned on the attachment surface, which is adhered to the user's target area 10, of the electrode band module 210, and may include at least one of hydrogel and hydrocolloid. Here, hydrogel and hydrocolloid can melt at temperatures ranging from 30° C. to 40° C. due to the user's body heat. For instance, the electrode pad 233 may have a thickness ranging from 30 µm to 60 µm. Alternatively, the electrode pad 233 may receive power wirelessly from the communication module 220.

For example, the thickness and amount of the electrode pad 233 can be varied depending on the amount of exudate from the wound at the user's target area 10. Typically, hydrocolloid dressing absorbs wound exudate through hydrophilic molecules. However, there is a limit in absorbing exudate, so there is a need to frequently exchange the hydrocolloid dressing when there is a significant amount of exudate. However, the present invention minimizes the exchange of the band due to saturation of exudate because the electrode pattern 232 evaporates the exudate through osmotic phenomena and heat generation. Additionally, as described above, the heat generated by the electrode pattern 232 can accelerate the melting rate of substances such as gelatin and hydrogel. So, the present invention can overcome the shortcomings of conventional bands through the combination of the electrode pattern 232 and the electrode pad 233.

For instance, the nanosome 231, the electrode pattern 232, and the electrode pad 233 can be varied in dissolution speed by the user's body heat. For example, the electrode pattern 232 may dissolve first, followed by the electrode pad 233, and the nanosome 231 dissolves finally. Accordingly, the nanosome 231, the electrode pad 233, and the electrode pattern 232 may be arranged in order of thickness. That is, the thickness can be: electrode pattern 232<electrode pad 233<nanosome 231.

The processor 240 senses whether the exudate at the user's target area 10 is in the supersaturated state or the unsaturated state, and controls the communication module 220 and the electrode module 230. Specifically, if sensing that the exudate is in the supersaturated state, the processor 240 can control the communication module 220 and the electrode module 230 to form the electric field at the user's target area 10.

Referring to FIGS. 1A and 3, the smart band according to an embodiment of the present invention may further include a ground connection unit 250, a feedback current measurement unit 261, a feedback voltage measurement unit 262, a humidity sensing unit 264, a charge measurement unit 265, a molybdenum sensing unit 266, and a triboelectric generator 270.

The ground connection unit 250 can be ground-connected to the user's target area 10. Here, the ground connection unit 250 can act as a positive pole, and the user's target area 10 can act as a negative pole. Alternatively, the ground connection unit 250 can act as a negative pole and the user's target area 10 can act as a positive pole.

The feedback current measurement unit 261 is electrically connected to the ground connection unit 250 and measures the feedback current entering and returning through the ground connection unit 250. In this instance, the processor 240 can determine the supersaturated state and the unsaturated state of the exudate at the user's target area 10 based on the measured feedback current. For example, if a feedback current value measured by the feedback current measurement unit 261 is zero or below a standard current, the processor 240 can determine the exudate at the user's target area 10 as being in the supersaturated state. Conversely, if the feedback current value is above the standard current, the processor 240 can determine as being in the unsaturated state. Furthermore, the standard current of the feedback current value may be set at 0.1 mA.

The feedback voltage measurement unit 262 is electrically connected to the ground connection unit 250 and measures the feedback voltage entering and returning through the ground connection unit 250. The processor 240 can determine the supersaturated state and the unsaturated state of the exudate at the user's target area 10 based on the measured feedback voltage. For example, if the feedback voltage value measured by the feedback voltage measurement unit 262 is zero or below a standard voltage, the processor 240 can determine the exudate at the user's target area 10 as being in the supersaturated state. Conversely, if the feedback voltage value is above the standard voltage, the processor 240 can determine the exudate as being in the unsaturated state. Additionally, the standard voltage of the feedback voltage may be set at 0.1 V.

It is possible to have any one of the feedback current measurement unit 261 and feedback voltage measurement unit 262, but the present invention is not limited thereto, and may have both of the feedback current measurement unit 261 and feedback voltage measurement unit 262.

For instance, if the state of the exudate determined by the feedback current measurement unit 261 and the state of the exudate determined by the temperature sensor 227 are different from each other, the processor 240 can re-measure the feedback current of the feedback current measurement unit 261 to reassess the supersaturated state and the unsaturated state of the exudate. Specifically, if the exudate's state is determined to be supersaturated by the feedback current measurement unit 261 and is determined to be unsaturated by the temperature sensor 227, the processor 240 can re-measure the feedback current to reassess the exudate's state. In addition, if the exudate's state is determined to be unsaturated by the feedback current measurement unit 261 and is determined to be supersaturated by the temperature sensor 227, the processor 240 can re-measure the feedback current of the feedback current measurement unit 261 to reassess the exudate's state.

Alternatively, if the state of the exudate determined by the feedback voltage measurement unit 262 and the state of the exudate determined by the temperature sensor 227 are different from each other, the processor 240 can re-measure the feedback voltage of the feedback voltage measurement unit 262 to reassess the supersaturated state and the unsaturated state of the exudate. Specifically, if the exudate's state is determined to be supersaturated by the feedback voltage measurement unit 262 and is determined to be unsaturated by the temperature sensor 227, the processor 240 can re-measure the feedback voltage to reassess the exudate's state. In addition, if the exudate's state is determined to be unsaturated by the feedback voltage measurement unit 262 and is determined to be supersaturated by the temperature sensor 227, the processor 240 can re-measure the feedback voltage of the feedback voltage measurement unit 262 to reassess the exudate's state.

The humidity sensing unit 264 is provided on the communication module 220 to sense the humidity at the target area 10. The processor 240 can verify the exudate at the user's target area 10 as the unsaturated state if the humidity sensed by the humidity sensing unit 264 is below a standard humidity level, and as the supersaturated state if the humidity is above the standard humidity level.

For instance, the humidity sensing unit 264 can be placed at one end of the communication module 220 connected to the nanosome 231 so as to be as close as possible to the user's target area 10. Therefore, the humidity sensing unit 264 can measure humidity of the user's target area 10 the most accurately.

For example, if the state of the exudate determined by the feedback current measurement unit 261 and the state of the exudate determined by the humidity sensing unit 264 are different from each other, the processor 240 can re-measure the feedback current of the feedback current measurement unit 261 to reassess the supersaturated state and the unsaturated state of the exudate. Specifically, if the exudate's state is determined to be supersaturated by the feedback current measurement unit 261 and is determined to be unsaturated by the humidity sensing unit 264, the processor 240 can re-measure the feedback current to reassess the exudate's state. In addition, if the exudate's state is determined to be unsaturated by the feedback current measurement unit 261 and is determined to be supersaturated by the humidity sensing unit 264, the processor 240 can re-measure the feedback current of the feedback current measurement unit 261 to reassess the exudate's state.

The charge measurement unit 265 is electrically connected to the ground connection unit 250 and can measure the charge characteristics of the target area 10 through the ground connection. The processor 240 can determine the exudate as being in the supersaturated state if the charge measured at the target area 10 is negative, and determine the exudate as being in the unsaturated state if the charge measured at the target area 10 is positive.

The triboelectric generator 270 is provided on the communication module 220 and can supply friction electricity generated due to friction by ultrasound irradiation to the communication module 220 as power.

Figure 6:
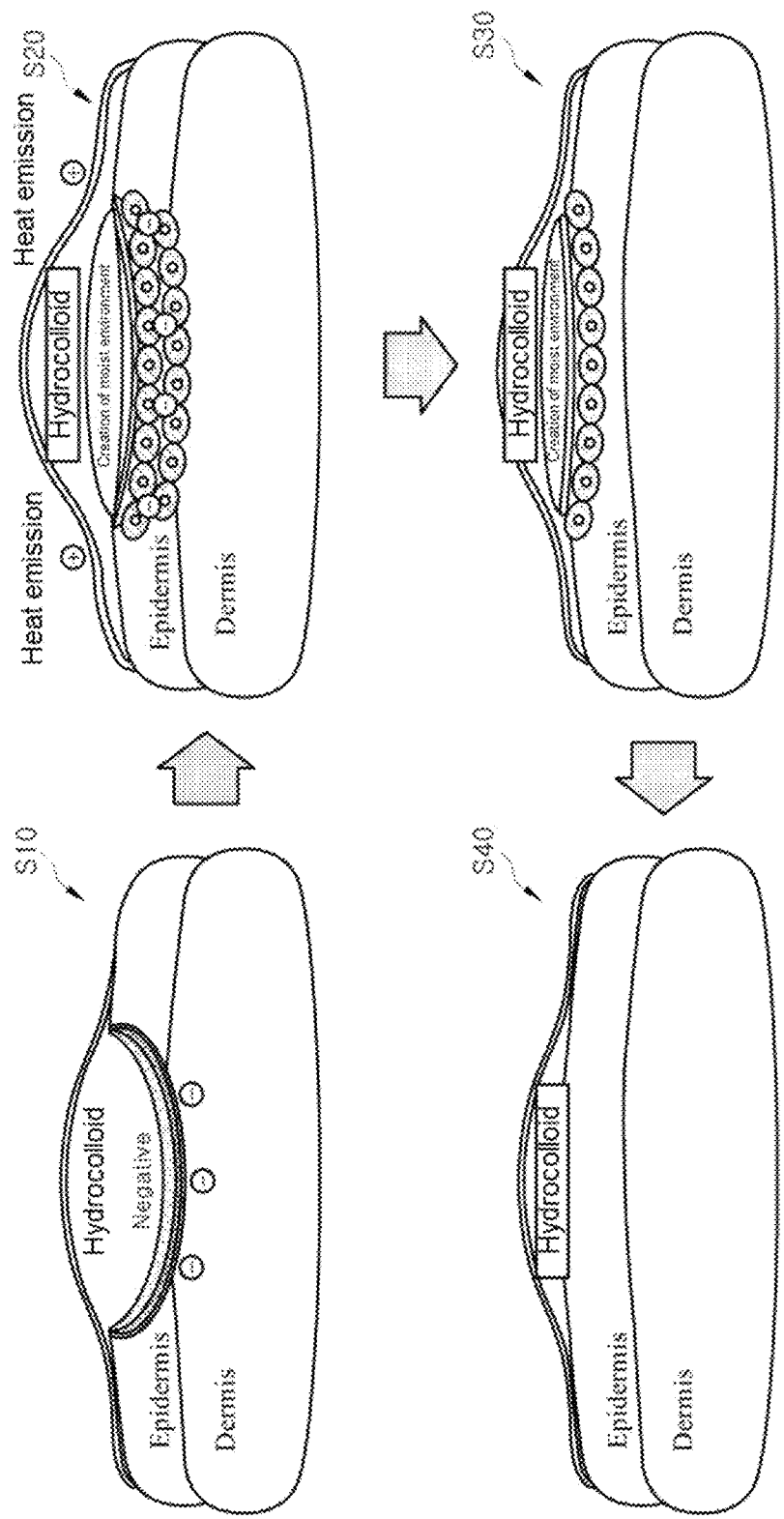
FIG. 6 is a schematic diagram illustrating a wound treatment process by the smart band for treating wounds and injuries capable of self-treatment according to the embodiment of the present invention.

FIG. 6 is a schematic diagram illustrating a wound treatment process by the smart band for treating wounds and injuries capable of self-treatment according to the embodiment of the present invention.

First, the smart band 200 for treating wounds and injuries is attached to the user's target area 10. In this instance, the electrode pattern 232 can be inserted into the wound at the target area 10, and the electric field created by the electrode pattern 232 supplies negative electric stimulation signals to the epidermis and the dermis to treat wounds. The signals stimulate growth factors, and the growth factors stimulate the granulation tissues in fibroblasts (refer to S10).

In this process, materials that absorb exudate and the melted time-sensitive materials of the electrode module 230 at the user's target area 10 are necessary. Hydrogel or hydrocolloid contained in the electrode pad 233 can be used to absorb the exudate. The hydrocolloid or hydrogel contained in the electrode pad 233 creates a moist environment while absorbing the exudate. When the time-sensitive material electrically stimulates the wound at the user's target area 10, heat is generated and the exudate is vaporized, and then, is expelled by the porous polyethylene attached to the hydrocolloid (or hydrogel). The vaporization process serves to reduce excessive exudate, and can apply electrical stimulation using the time-sensitive material, thereby quickly mitigating heat generated during the process of accelerating and recovering wounds.

Meanwhile, the dissolution speed of the hydrocolloid of the electrode pad 233, which dissolves by the user's body temperature, is accelerated, and collagen proteins such as pectin and gelatin contained in the electrode pad 233 interact with the wound, causing fibroblasts to be transformed into new capillaries. Additionally, since the time-sensitive material is absorbed by the user, the electrical stimulation applied by the electrode pattern 232 to the user's target area 10 is significantly reduced from the intermediate stage onward. The above results in an effect similar to 'suturing', thereby enhancing resistance to treatment complication (infection) and improving functional and aesthetic aspects. (Refer to S20)

Subsequently, the processor 240 senses the supersaturated state and the unsaturated state of the exudate at the user's target area 10 and decides whether to form an additional electric field at the target area 10. Specifically, if the processor 240 determines the exudate is in the supersaturated state, the processor 240 controls the communication module 220 and the electrode module 230 to form an additional electric field. As a result, the exudate at the user's target area 10 is vaporized, thus preventing delay in wound treatment caused by the accumulation of exudate. (refer to S30)

For example, the processor 240 initially determines that the exudate is in the supersaturated state by one of the feedback current measurement unit 261, the feedback voltage measurement unit 262, and the charge measurement unit 265, and then verifies the supersaturated state by the temperature sensor 227 or the humidity sensing unit 264.

Alternatively, the processor 240 initially determines that the exudate is in the supersaturated state by two or more of the feedback current measurement unit 261, the feedback voltage measurement unit 262, and the charge measurement unit 265, and then verifies the supersaturated state by the temperature sensor 227 or the humidity sensing unit 264.

Next, the molybdenum sensing unit 266 senses the molybdenum in the user's target area 10 to confirm whether molybdenum components of the electrode pattern 232 remains in the user's target area 10. Herein, if determining that the exudate is in the unsaturated state, the processor 240 can control the communication module 220 and the electrode module 230 to form the electric field for removing molybdenum from the user's target area 10. In this regard, the melting rate of molybdenum can be accelerated by the user's body heat. (refer to S40)

For example, upon removal of the smart band, the electrode band module 210 and the communication module 220 can be simultaneously separated from the user's target area 10 or, after the communication module 220 alone is separated and the electrode module 230 is completely melt by the user's body heat, the electrode band module 210 can be separated from the user's target area 10.

Specifically, in the state in which the electrode module 230 located at the user's target area 10 is completely melted by the user's body heat, the electrode band module 210 and the communication module 220 can be separated together from the user's target area 10.

Furthermore, in the state in which the electrode module 230 located at the user's target area 10 is not completely melted by the user's body heat, after the communication module 220 alone is separated and the electrode module 230 is completely melt by the user's body heat, the electrode band module 210 can be separated from the user's target area 10.

Meanwhile, if the state that hydrogel of the electrode module 230 is not completely melted persists for a long period of time, the processor can control the communication module 220 and the electrode module 230 to form the electric field for the removal of the hydrogel of the electrode module 230 at the user's target area 10.

Figure 7:
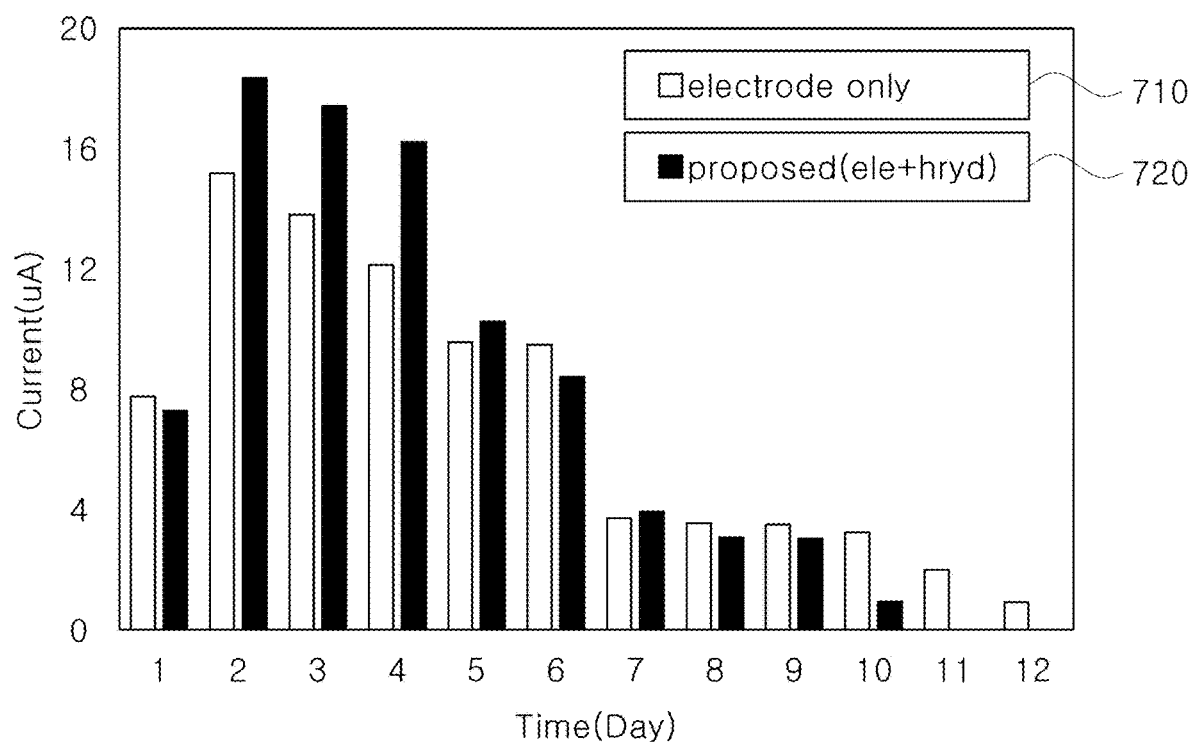
FIG. 7 is a graph for explaining test results of the current transmission rate of the smart band for treating wounds and injuries capable of self-treatment according to the embodiment of the present invention.

FIG. 7 is a graph for explaining test results of the current transmission rate of the smart band for treating wounds and injuries capable of self-treatment according to the embodiment of the present invention.

As wound treatment progresses, the current used for treating the wound tends decreases. This is why as the wound is treated, the internal current of the body increases and resistance to the externally provided current increases, and as the melting degree of time-sensitive biometric mimicking elements for treating wounds increases, the efficiency of current transfer decreases. Additionally, because the exudate from the wound is highly hydrophilic, current transfer is high, so the exudate decreases with wound treatment, and the current transfer effect also decreases.

The graph in FIG. 7 shows the results of testing the current transfer rate of the wound in two ways. The two methods are: (710) using electrodes only; and (720) using electrodes and hydrocolloid. Here, the method (720) of using electrodes and hydrocolloid shows a faster treatment effect. Initially, there is little difference due to a small amount of exudate, but after 24 hours (1 day), the exudate from the wound increases rapidly. The smart band (120) for treating wounds disclosed herein uses the method (720) of using electrodes and hydrocolloid, and with the progress of wound treatment, extrude in which hydrocolloid is liquefied is created, thus showing a high current transfer rate.

Figure 8:
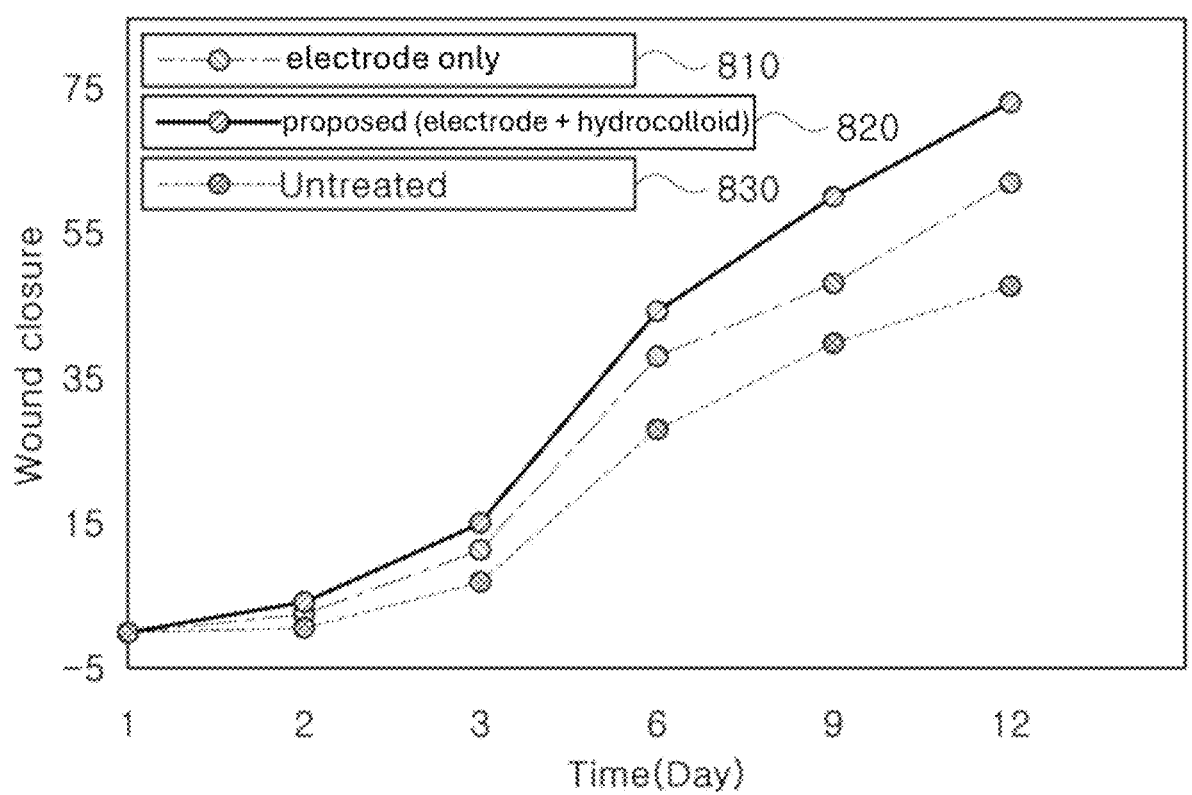
FIG. 8 is a graph for explaining test results of the wound treatment effect of the smart band for treating wounds and injuries capable of self-treatment according to the embodiment of the present invention.

FIG. 8 is a graph for explaining test results of the wound treatment effect of the smart band for treating wounds and injuries capable of self-treatment according to the embodiment of the present invention.

The graph in FIG. 8 shows the test results of three different methods used for treating wounds. The three methods are: (810) using electrodes only; (820) using electrodes and hydrocolloid method; and (830) natural treatment.

The natural treatment method (830) shows effectiveness up to 75% of skin tension, so the test compares the wound recovery power of 75% in the natural treatment method (830) as a baseline. However, since the proposed method (820) of using electrodes and hydrocolloid demonstrates effectiveness up to 72-73% over 12 days, the comparison was conducted during the same period of 12 days. In general, the method (820) of using electrodes and hydrocolloid showed wound recovery power up to 85%, and the method of using electrodes only was conducted in a way to minimize inflammatory reactions by minimizing external viral penetration in an aseptic chamber, but there was still the influence of air-induced wound crusting. The above factors were reflected to the test, and the test was conducted days, resulting in verifying the superiority of the method (820) of using electrodes and hydrocolloid in wound recovery power.

According to the present invention, the smart band for treating wounds and injuries and the smart band control system including the same can accelerate oxidation and reduction reactions by applying electrical stimulation to wounds, and vaporize supersaturated invasive substances at a user's target area, thereby preventing the delay in wound recovery caused by the supersaturated invasive substances at the user's target area.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

NRF of Korea (1711200883): This research was conducted as part of the Electronic Medicine Technology Development Project, supported by the National Research Foundation of Korea with funding from the Ministry of Science and ICT. (Sub-project number: 2022M3E5E9016662)

This research was conducted with the support of the KEIT, funded by the Ministry of Trade, Industry and Energy of the Korean government in 2023. (1415187321/20025736, Development of Communication SoC and Platform for Implantable Electronic Medicines in 2023).

What is claimed is:

1. A smart band for treating wounds and injuries capable of self-treatment comprising:
    an electrode band module configured to be attached to a target area of a user;
    a communication module connected to the electrode band module and having a wireless power transmission function;
    an electrode module arranged on the electrode band module, made of a time-sensitive material, and forming an electric field that electrically stimulates the target area and evaporates exudate of the target area by the power supplied from the communication module; and
    a processor sensing a supersaturated state or an unsaturated state of the exudate, and controlling the communication module and the electrode module,
    wherein the processor, upon determining that the exudate is in the supersaturated state, controls the communication module and the electrode module to form the electric field,
    wherein the electrode module includes:
    nanosomes receiving power from the communication module;
    an electrode pattern forming the electric field by the power transferred from the nanosomes; and
    an electrode pad coupled to the nanosomes and the electrode pattern, provided on an attachment surface of the electrode band module, and including at least one of hydrogel and hydrocolloid, and
    wherein the nanosomes comprise lipase enzyme.

2. The smart band according to claim 1, further comprising:
    a ground connection unit ground-connected to the target area; and
    a feedback current measurement unit electrically connected to the ground connection unit, and measuring a feedback current entering and returning to the ground connection unit,
    wherein the processor determines the supersaturated state or the unsaturated state of the exudate based on the feedback current measured by the feedback current measuring unit.

3. The smart band according to claim 2, further comprising:
    a temperature sensor provided on the communication module to measure the temperature of the target area,
    wherein the processor, when a temperature measurement value measured by the temperature sensor exceeds a reference temperature, verifies the exudate as being in the supersaturated state, and when the temperature measurement value is below the reference temperature, verifies the exudate as being in the unsaturated state.

4. The smart band according to claim 3, wherein when the state of the exudate determined by the feedback current measurement unit differs from the state determined by the temperature sensor, the processor re-measures the feedback current through the feedback current measurement unit to re-determine the supersaturated state or the unsaturated state of the exudate.

5. The smart band according to claim 2, further comprising:
    a humidity sensing unit sensing the humidity of the target area,
    wherein the processor verifies the exudate as being in the unsaturated state when the humidity sensed by the humidity sensing unit is below a reference humidity, and verifies the exudate as being in the supersaturated state when the humidity sensed exceeds the reference humidity.

6. The smart band according to claim 5, wherein when the state of the exudate determined by the feedback current measurement unit differs from the state determined by the humidity sensing unit, the processor re-measures the feedback current through the feedback current measurement unit to re-determine the supersaturated state or the unsaturated state of the exudate.

7. The smart band according to claim 2, further comprising:
    a charge measurement unit electrically connected to the ground connection unit and measuring a charge characteristic the target area through the ground connection unit,
    wherein the processor, when the charge characteristic measured by the charge measurement unit at the target area is negative, determines the exudate as being in the supersaturated state, and when the charge characteristic measured by the charge measurement unit at the target area is positive, determines the exudate as being in the unsaturated state.

8. The smart band according to claim 7, wherein the electrode pattern includes molybdenum.

9. The smart band according to claim 8, wherein the molybdenum is formed of a thin film having a thickness of 0.1 µm to 10 µm, and has a cross-sectional area of less than 10% of the target area.

10. The smart band according to claim 8, further comprising:
    a molybdenum sensing unit arranged on the communication module to sense the molybdenum at the target area,
    wherein the processor, upon determining that the exudate is in the unsaturated state, controls the communication module and the electrode module to form an electric field to remove the molybdenum at the target area.

11. The smart band according to claim 1, further comprising:
    a triboelectric generator arranged on the communication module to supply friction electricity generated due to friction by ultrasound irradiation to the communication module as power.

12. The smart band according to claim 1, further comprising:
    a ground connection unit ground-connected to the target area; and a feedback voltage measurement unit electrically connected to the ground connection unit to measure a feedback voltage entering and returning to the ground connection unit, wherein the processor determines the supersaturated state or the unsaturated state of the exudate based on the feedback voltage measured by the feedback voltage measuring unit.

13. The smart band according to claim 1, wherein when the smart band is removed, the electrode band module and the communication module are simultaneously separated from the target area or, after the communication module alone is separated and the electrode module is configured to be completely melt by a body heat of the user, the electrode band module is separated.

* * * * *